(12) United States Patent
Li et al.

(10) Patent No.: US 6,214,777 B1
(45) Date of Patent: Apr. 10, 2001

(54) ANTIMICROBIAL LUBRICANTS USEFUL FOR LUBRICATING CONTAINERS, SUCH AS BEVERAGE CONTAINERS, AND CONVEYORS THEREFOR

(75) Inventors: Minyu Li, Oakdale, MN (US); Kim L. Person-Hei, Baldwin, WI (US); Bruce R. Cords, Inver Grove Heights, MN (US); Keith D. Lokkesmoe, Savage, MN (US); Joy G. Herdt, Hastings, MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 09/404,813

(22) Filed: Sep. 24, 1999

(51) Int. Cl.[7] ............................................ C10M 173/02
(52) U.S. Cl. ..................... 508/388; 508/421; 508/539; 508/547; 508/564; 428/35.7; 428/500; 428/543
(58) Field of Search .................................. 508/388, 539, 508/564

(56) References Cited

U.S. PATENT DOCUMENTS

| | | |
|---|---|---|
| 3,624,260 | 11/1971 | Peterson ................. 252/49.8 |
| 3,642,691 | 2/1972 | Worrel ................. 260/45.85 |
| 3,707,501 | 12/1972 | Gentit et al. ................. 252/78 |
| 3,954,866 | 5/1976 | Frank et al. ................. 260/568 |
| 3,987,098 | 10/1976 | Frank et al. ................. 260/568 |
| 4,406,801 | 9/1983 | Onopchenko et al. ......... 252/46.7 |
| 4,462,935 | 7/1984 | Onopchenko et al. ......... 260/429.7 |
| 4,521,321 | 6/1985 | Anderson et al. ................. 252/49.3 |
| 4,806,256 | 2/1989 | Rose et al. ................. 252/71 |
| 4,874,526 | 10/1989 | Grade et al. ................. 210/697 |
| 5,073,280 | * 12/1991 | Rossio et al. ................. 252/49.3 |
| 5,240,709 | 8/1993 | Pilling et al. ................. 424/420 |
| 5,244,589 | 9/1993 | Liu et al. ................. 252/34 |
| 5,391,308 | 2/1995 | Despo ................. 252/32.5 |
| 5,416,210 | * 5/1995 | Sherba et al. ................. 540/609 |
| 5,441,654 | 8/1995 | Rossio ................. 252/49.3 |
| 5,462,681 | * 10/1995 | Gutzmann et al. ................. 252/11 |
| 5,510,045 | 4/1996 | Remus ................. 252/49.3 |
| 5,534,172 | 7/1996 | Perry et al. ................. 508/156 |
| 5,559,087 | * 9/1996 | Halsrud et al. ................. 508/579 |
| 5,723,418 | * 3/1998 | Person Hei et al. ................. 508/511 |
| 5,863,874 | 1/1999 | Person Hei et al. ................. 508/521 |
| 5,874,476 | 12/1999 | Hsu et al. ................. 514/640 |
| 5,922,745 | 7/1999 | McCarthy et al. ................. 514/372 |
| 5,925,601 | * 7/1999 | McSherry et al. ................. 508/425 |
| 5,932,526 | * 8/1999 | Person Hei et al. ................. 508/559 |

FOREIGN PATENT DOCUMENTS

| | | |
|---|---|---|
| 2082994 | 11/1992 | (CA) . |
| 470280 | 12/1992 | (EP) . |
| 2567128 | 1/1986 | (FR) . |
| 4094832 | 3/1992 | (JP) . |
| 02616 | 2/1996 | (WO) . |
| 14092 | 5/1996 | (WO) . |

* cited by examiner

Primary Examiner—Ellen M. McAvoy
(74) Attorney, Agent, or Firm—Shanks & Herbert

(57) ABSTRACT

A lubricant composition comprising a lubricating agent and a quaternary phosphonium compound is useful as a conveyor, container or beverage lubricant.

28 Claims, No Drawings

ANTIMICROBIAL LUBRICANTS USEFUL FOR LUBRICATING CONTAINERS, SUCH AS BEVERAGE CONTAINERS, AND CONVEYORS THEREFOR

BACKGROUND OF THE INVENTION

1. Field of the Invention

The present invention relates to antimicrobial lubricant compositions, and to their use, for example, to treat or lubricate containers and/or conveyor systems for containers. The invention also relates to containers and conveyor systems treated with an antimicrobial lubricant.

2. Description of Related Art

Containers are receptacles in which materials are or will be held or carried. Containers are commonly used in the food or beverage industry to hold food or beverages. Often lubricants are used in conveying systems for containers, to ensure the appropriate movement of containers on the conveyor.

In the commercial distribution of many products, including most beverages, the products are packaged in containers of varying sizes. The containers can be in the form of cartons, cans, bottles, Tetra Pak® packages, waxed carton packs, and other forms of containers. In most packaging operations, the containers are moved along conveying systems, usually in an upright position, with the opening of the container facing vertically up or down. The containers are moved from station to station, where various operations, such as filling, capping, labeling, sealing, and the like, are performed.

Containers, in addition to their many possible formats and constructions, may comprise many different types of materials, such as metals, glasses, ceramics, papers, treated papers, waxed papers, polymeric materials, composites, and layered structures. Any desired polymeric materials can be used, such as polyolefins, including polyethylene, polypropylene, polystyrene, and mixtures thereof, polyesters such as polyethylene terephthalate (PET) and polyethylene naphthalate (PEN) and mixtures thereof, polyamides, polycarbonates, and the like. Also, containers, such as bottles, with layered, laminated films, formed from PEN, PET, copolymers of the monomers that form PEN and PET, or mixtures thereof, can be used. Containers can be coated with internal and/or external coatings, formed by, for example, thermosetting or UV curing, such as epoxy polymers cured with amines.

Lubricating solutions are often used on conveying systems during the filling of containers, for example, with beverages. There are a number of different properties that are desirable for such lubricants. For example, the lubricant should provide an acceptable level of lubricity for the system. It is also desirable that the lubricants have a viscosity which allows it to be applied by conventional pumping and/or application apparatus, such as by spraying, roll coating, wet bed coating, and the like, commonly used in the industry.

In the beverage industry, there is a high demand for conveyor lubricants that are beverage compatible, and have both lubricative and antimicrobial properties. By beverage compatible, is meant that the lubricant is compatible with the beverage so that it does not form solid deposits when it accidentally contacts spilled beverages on the conveyor system. This property is important since the formation of deposits on the conveyor system may change the lubricity of the system and could require shut-down of the equipment to facilitate cleaning.

Carbonated beverages contain ingredients with anionic charges, such as colors and flavors, which are held in solution through emulsification. Given this generally negative charge, the cationic constituents of a synthetic lubricant, such as quaternary ammonium salts, amines, and ether amines, may react with the beverages to form precipitates. The precipitates accumulate on conveyors, housing, and floors as a tenacious soil, and may cause a halt in production to facilitate cleaning.

If the lubricant is for use on PET bottle lines, then good compatibility with PET is desired. Currently, containers, including PET bottles, and/or the conveying system are often coated with an aqueous-based lubricant to provide lubricity to the container so that it can more easily travel down a conveyor system. Many currently used aqueous-based lubricants are disadvantageous because they are incompatible with many beverage containers, such as PET and other polyalkylene terephthalate containers, and may lead to stress cracking and rupture of the PET bottles.

A sufficient lubrication of the conveyor ensures a proper movement of containers along the conveyor system. Lubricants having fatty acids are known to have good lubricity, especially for metal surface lubrication. However, fatty acids generally need to be neutralized in order to have a good solubility in water. The use of sodium or potassium hydroxide as the neutralizing agent, in fatty acid containing lubricants, has been found to increase the alkalinity of the lubricant, and to thus contribute and promote the stress cracking in PET containers.

PET bottle manufacturers and soft drink bottlers have come to a growing understanding that alkalinity is one root cause of stress crack failure of pressurized PET containers. As a result, alkalinity limits of less than 100 ppm as $CaCO_3$ have been proscribed for any water or lubricant that comes into contact with the PET article. This development has led to the obsolescence of many longstanding lubricant technologies. For example, as discussed above, fatty acid based lubricants require neutralization with alkaline materials in order to achieve water solubility of the product. The resultant alkalinity of fatty acid products as applied to the conveyors and bottles often exceed the current alkalinity limit. It is also believed that PET stress cracking can be promoted by certain types of lubricant additives, such as alkyl(ether)(di)amines and quaternary ammonium salts.

Lubricants generally contain an antimicrobial agent to reduce the growth of microbes. Antimicrobial agents are agents that eliminate or inactivate microorganisms, or prevent, frustrate, or reduce the growth of microorganisms. Because conveyor lubricants are often used at low concentration, the antimicrobial agent should preferably be highly water soluble and effective at very diluted solutions. Although some types of alcohols, amines, and quaternary ammonium salts are known to satisfy these requirements, they are often disadvantageous because their incompatibility with PET containers can enhance the PET stress cracking.

Also, there are generally known antimicrobial, beverage compatible conveyor lubricants, that contain a quaternary ammonium antimicrobial agent and phosphate esters. Such compositions often are disadvantageous because certain ratios of the components may contribute to soiling due to the mixing of quaternary ammonium compound with soft drink spillage.

SUMMARY OF THE INVENTION

Therefore, there is a need to provide an alternative to currently available lubricants for containers and conveyors for the containers, that overcome one or more of the disadvantages of currently used lubricants. For example, it is desired to provide a lubricant composition with reduced alkalinity, good PET compatibility such that stress cracking of PET is limited, superior lubricity for all types of containers, a stable product shelf life, improved beverage compatibility and effective antimicrobial properties.

It was also an object of the invention to provide methods of lubricating containers, such as beverage containers, that overcome one or more of the disadvantages of current methods.

In accordance with the objectives, there has been provided in accordance with the present invention, a beverage lubricant composition comprising a lubricant agent and a quaternary phosphonium compound.

In accordance with these objectives, there is also provided a container or a conveyor for a container whose surface is coated at least in part with a lubricant composition comprising a lubricant agent and a quaternary phosphonium compound.

There is also provided in accordance with the invention, a process for lubricating a container, comprising applying to a surface of the container, such a lubricant composition.

There is also provided in accordance with the invention, a process for lubricating a conveyor system used to transport containers, comprising applying such a lubricant composition to the conveying surface of a conveyor, and then moving containers on the conveyor.

There is also provided in accordance with the invention, a conveyor used to transport containers, which is coated on the portions that contact the container with such a lubricant composition.

There is also provided a lubricant composition, such as for a beverage, comprising a lubricant agent and a sulfonium or iodonium compound.

Further objects, features, and advantages of the invention will become apparent from the detailed description that follows.

DETAILED DESCRIPTION OF PREFERRED EMBODIMENTS

The present invention relates to a lubricating composition comprising a quaternary phosphonium compound. Any desired quaternary phosphonium compound may be used. Such compounds may have the general structure $[R_1R_2R_3R_4P]_n^+X^{n-}$ in which n is a number from 1–4 and corresponds to the valence of the anion $X^{n-}$. $R_1$, $R_2$, $R_3$, and $R_4$ are the same or different groups. The R groups are independently organic groups, such as substituted or unsubstituted alkyl or cycloalkyl and substituted or unsubstituted aryl. For example, $R^1$, $R^2$, $R^3$, and $R^4$ can be independently a $C_{1-24}$ aliphatic group, a $C_{1-4}$ hydroxyaliphatic group, benzyl, $C_{1-24}$ alkyl benzyl, or halo benzyl, and X- represents an anion capable of imparting water solubility or dispersibility to the compound such as chloride, bromide, iodide, sulfate, methylsulfate, and others. This anion is linked to the nitrogen through an electrovalent bond.

The hydrocarbon substituents $R^1$, $R^2$, $R^3$, and $R^4$ may be alike or different, substituted or unsubstituted, branched or unbranched, and saturated or unsaturated. In somewhat greater detail, the hydrocarbon substituents $R^1$, $R^2$, $R^3$, and $R^4$ may be independently selected from hydrocarbon groups including specifically, but not exclusively: lower alkyl groups such as methyl, ethyl, propyl and butyl; higher alkyl groups such as pentyl, hexyl, heptyl, 2-ethylhexyl, octyl, isooctyl, nonyl, decyl, unidecyl, dodecyl, tetradecyl, and eicosyl; substituted lower alkyl groups such as hydroxyethyl and hydroxypropyl; lower alkenyl groups such as ethenyl, propenyl, and butenyl; lower alkynyl groups such as ethynyl, propynyl, and butynyl; cycloalkyl groups such as cyclohexyl; aryl groups such as benzyl, phenyl and naphthyl; and aralkyl/alkaryl groups such as tolyl, xylyl, alkyl substituted benzyl, and alkylnaphthyl.

Non-limiting examples of useful phosphonium salts are the compounds described in Canadian Patent No. 2,082,994, U.S. Pat. No. 4,874,526, and European Patent No. 322,578, each which is incorporated by reference in its entirety. Examples of useful phosphonium salts include tetrakis (hydroxymethyl) phosphonium sulfate, tetrabutyl phosphonium bromide, tetrabutyl phosphonium chloride, tributyl (tetradecyl) phosphonium chloride, trioctyl (octadecyl) phosphonium iodode, and tetrakis (hydroxymethyl) phosphonium chloride. Particularly preferred is tetrakis (hydroxymethyl) phosphonium sulfate. A particularly useful compound is Tolcide PS 200 or 75 available from Albright & Wilson.

The lubricant composition includes a quaternary phosphonium compound as an antimicrobial agent, in an amount effective to provide antimicrobial properties. Antimicrobial agents are agents that eliminate or inactivate microorganisms, or prevent, frustrate, or reduce the growth of microorganisms. The phosphonium can be present in an amount of from about 0.5 to about 25 percent by weight, preferably 1 to 15 percent by weight, more preferably 2 to 10 percent by weight, most preferably about 4% by weight, based on the weight of the lubricant composition.

It has been found that a lubricant with an adequate biocidal activity can be obtained by incorporation of the quaternary phosphium compound. Moreover, unlike quaternary ammonium salts and other microbial surfactants, the quaternary phosphoniums are believed to be inert to PET bottle cracking. This provides the added benefit of improving the stability of pressurized PET bottles. Additionally, it has been found that the lubricant containing quaternary phosphonium does not form a soil with many types of beverages, such as carbonated beverages. The compound is also compatible with the usual components of lubricant compositions, such as those described below.

In place of or in addition to the phosphonium compounds, other onium salts, such as sulfonium and iodonium compounds can be used, in amounts analogous to those of the phosphoniums. It is believed that the sulfonium and iodonium compound can function as antimicrobial agents in the lubricant compositions. Non-limiting examples of useful iodonium and sulfonium salts include diaryliodonium and triarylsulfonium salts such as diphenyl iodonium chloride, diphenyl iodonium iodide, triphenyl sulfonium hexafluorophosphate, and triphenyl sulfonium tetrafluoroborate.

Any desired lubricating agent can be used in the composition. Examples include water, amines such as fatty amines, fatty acids, sarcosinates, phosphate esters, water-soluble or water dispersible homopolymers or copolymers of (alkoxy) alkylene glycols, alcohol ethoxycarboxylates such as Neodox available from Hickson Danchem, and water soluble or water dispersible oils.

The lubricating agent or a combination thereof, is used in an amount to provide effective lubricity to the composition. For example, 1–95 percent by weight, preferably 3–60, more preferably 6–50 percent by weight of lubricating agents can be included. If fatty acid is used, it can be in an amount from about 0.1 to about 20 percent by weight, preferably 0.25 to 12 percent by weight, more preferably 0.5 to 7 percent by weight, most preferably about 2.5% by weight. If a phosphate ester is used, it can be in an amount of from about 1 to about 50 percent by weight, preferably 2 to 30 percent by weight, more preferably 5 to 25 percent by weight, most preferably about 12 percent by weight of the composition.

It has been found that the lubricity of the lubricant compositions including quaternary phosphonium compounds on metal conveyor systems can often be improved by use of a non-neutralized fatty acid. It was unexpectedly found that such fatty acids not only improve lubricity, but lower alkalinity of the lubricant composition without destroying the product solution stability, that is, phase separation does not occur. The fatty acid is compatible with PET, but can also be used, for example, as a universal lubricant for other containers, including glass, aluminum, and paperboard containers. The fatty acid is also compatible with many biocides, and is non-soiling in the event of contamination with spilled food products.

In conventionally used lubricant compositions, if a fatty acid is used as a lubricant, it is often necessary to neutralize the fatty acid to make it water soluble. This neutralization disadvantageously increases the alkalinity of the composition. It has been found, that in the present compositions, it is not necessary to neutralize the fatty acid, thereby allowing the composition to have a pH of about 7 or lower. But it is acceptable to use neutralized fatty acids as well as partially neutralized fatty acids in the composition.

A wide variety of carboxylic or fatty acids may be usefully employed in the antimicrobial lubricant compositions of the invention. Those acids found to provide effective lubricity include those having the general formula RCOOH wherein R represents an aliphatic group having from about 5 to about 23 carbon atoms (fatty acids having about 6 to 24 carbon atoms). The aliphatic group may be branched or unbranched and saturated or unsaturated, but is preferably a straight chain alkyl group. Preferred carboxylic acids include the $C_{10-18}$ fatty acids and mixtures thereof.

Specific examples of suitable carboxylic acids include such saturated fatty acids as enanthic (heptanoic) ($C_7$), caprylic (octanoic) ($C_8$), pelargonic (nonanoic) ($C_9$), capric (decanoic) ($C_{10}$), undecyclic (undecanoic) ($C_{11}$), lauric (dodecanoic) ($C_{12}$), trideclic (tridecanoic) ($C_{13}$), myristic (tetradecanoic) ($C_{14}$), palmitic (hexadecanoic) ($C_{16}$), stearic (octadecanoic) ($C_{18}$), arachidic (eicosanoic) ($C_{20}$), behenic (docosanoic) ($C_{22}$), and lignoceric (tetracosanoic) ($C_{24}$); monounsaturated fatty acids such as lauroleic ($C_{12}$), myristoleic ($C_{14}$), palmitoleic ($C_{16}$), oleic ($C_{18}$), gadoleic ($C_{20}$), and brassidic ($C_{22}$); polyunsaturated fatty acids such as linoleic (di-unsaturated $C_{18}$), and linolenic (tri-unsaturated) ($C_{18}$), and linolenic (tri-unsaturated $C_{18}$); and substituted fatty acids such as ricinoleic (hydroxy-substituted $C_{18}$), etc.

Mixed fatty acids may be employed in the antimicrobial lubricant composition of the invention such as those derived from fats and oils. Coconut oil fatty acids are particularly useful in the antimicrobial lubricant compositions of the invention because of their ready availability and superior lubricating properties. Coconut oil fatty acids include major fractions of lauric and myristic acids and minor fractions of palmitic, stearic, oleic and linoleic acids. Tall oil fatty acids, obtained as a byproduct of the paper industry from the tall oil recovered from pine wood black liquor, are also preferred fatty acids for use in the antimicrobial lubricant composition of the invention. Tall oil fatty acids include major fractions of oleic and linoleic acids and minor fractions of palmitic, stearic, and isotearic acids.

In a preferred embodiment, a fatty acid is used in combination with a phosphate ester. Any desired phosphate ester can be used (alone or with a fatty acid). Examples of useful phopshate esters are those available under the Rhodafac tradename from Rhone-Poulenc and Emphos tradename from Witco Corporation.

Any desired amine lubricating agent can be used. Useful amines have the formula $N(R^7)_3$, wherein $R^7$ can be hydrogen, a $C_{1-20}$ aliphatic group, an aryl group, an alkaryl group, and various halo, nitro, sulfo, and hydroxyl substituted forms thereof. Representative examples of suitable amines include methyl amine, dimethyl amine, ether amine, ethylene amine, diethylene amine, aniline, chloroaniline, morpholine, pyridine, 2-ethylhexyl amine, didodecyl amine, hydroxyethyl amine, dihydroxyethyl amine, trimethyl amine, diethyl methyl amine, dodecyl dimethyl amine, di(aminoethyl) dodecyl amine, imidazoline, etc.

Useful amine compounds also include diamines (secondary amines containing one amine substituent) having the general formula:

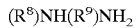

$(R^8)NH(R^9)NH_2$ wherein $R^8$ is a $C_{8-24}$ aliphatic group and $R^9$ is a $C_{1-20}$ alkylene group. Most preferably $R^8$ is a $C^{12}$–$C^{20}$ alkyl group and $R_9$ is a $C_{1-5}$ alkylene. Examples of useful diamines represented by the general formula $(R^8NH(CH_2)_{1-20}NH_2$ wherein $R^8$ is a $C_{10-24}$ aliphatic group includes N-coco-alkyl-trimethylene diamine, N-oleyl-alkyl-trimethylene diamine, N-tallow-alkyl-trimethylene diamine, and the like.

Also useful are ether amines of the general formula $R^8$—O—NH—$R^9$—$NH_2$, where the ariables are as defined above. Examples of useful ether amines include 1,3 propane iamine N-dodecyloxypropyl amine.

The lubricating agent can be a single component or a blend of materials from the same or different type or class of lubricant. Any desired ratio of the two or more lubricating agents can be used so long as the desired lubricity is achieved. The lubricants can be in the form of a fluid, solid, or mixture of two or more miscible or non-miscible components such as solid particles dispersed in a liquid phase.

The lubricant composition of the invention can include any other desired agents, such as neutralizing agents, surfactants, water, and water-conditioning agents.

Any desired neutralizing agent can be used. Useful neutralizing agents include the alkaline metal hydroxides and ammonium salts such as potassium hydroxide and sodium hydroxide. Other preferred neutralizing agents are alkyl amines, which may be primary, secondary or tertiary such as monoethanolamine, diethanolamine and triethanolamine. Other useful amines for neutralization include amino-methyl proponal, dimethyl decyl amine, octyl amine, alkyl propylene amines, such as n-coco-1,3 diaminopropane, N-tallow1,3 diaminopropane and ethoxylated amines such as ethoxylated coconut amine.

Generally the neutralizing agent is present in amount to adjust the pH of the composition to a range of about 3 to about 9.5, preferably 4.5 to 8.0, and more preferably in the range of 5.5 to 7.5.

The lubricant compositions of the invention optionally, but preferably, may further include a surfactant. The surfactant functions as an adjuvant to increase detergency and lubricity. Compounds which may be used as surfactants in the invention include, nonionic surfactants, amphoteric surfactants, anionic surfactants, and cationic surfactants among other compounds. Any desired surfactant can be used, in an amount effective to improve detergency and/or lubricity.

Anionic surfactants are generally those compounds containing a hydrophobic hydrocarbon moiety and a negatively charged hydrophilic moiety. Typical commercially available products provide either a carboxylate, sulfonate, sulfate or phosphate group as the negatively charged hydrophilic moiety. Any commercially available anionic surfactants may be employed in the lubricant composition of the invention.

Nonionic surfactants are generally hydrophobic compounds that bear essentially no charge and exhibit a hydrophilic tendency due to the presence of oxygen in the molecule. Nonionic surfactants encompass a wide variety of polymeric compounds which include specifically, but not exclusively, ethoxylated alkylphenols, ethoxylated aliphatic alcohols, ethoxylated amines, ethoxylated ether amines, carboxylic esters, carboxylic amides, ether carboxylates, and polyoxyalkylene oxide block copolymers. Any desired nonionic surfactant can be used.

Particularly suitable nonionic surfactants for use in the lubricant composition of the invention are the alkoxylated (preferably ethoxylated) alcohols having the general formula $R^{10}O((CH_2)_mO)_n$ wherein $R^{10}$ is an aliphatic group having from about 8 to about 24 carbon atoms, m is a whole number from 1 to about 5, and n is a number from 1 to about 40 which represents the average number of ethylene oxide groups on the molecule.

Nonionic surfactants are especially useful and can be used in an amount of about 0.5 to about 30 percent, preferably 1 to 15, more preferably 2 to 10, and most preferably about 5 percent by weight of the composition.

Cationic surfactants are also useful in the invention and may also function as an additional antimicrobial. Typical examples include amineoxides and quaternary ammonium chloride surfactants such as n-alkyl ($C_{12-18}$) dimethyl benzyl ammonium chloride, n-alkyl ($C_{14-18}$) dimethyl benzyl ammonium chloride, n-tetradecyl dimethyl benzyl ammonium chloride monohydrate, and n-alkyl ($C_{12-14}$) dimethyl 1-naphthylmethyl ammonium chloride. Also, non-benzyl compounds such as didecyl dimethyl ammonium chloride and compounds with bromide counter ions such as cetyltriamonium bromide can be used.

Amphoteric surfactants, surfactants containing both an acidic and a basic hydrophilic group, can be used in the invention. Amphoteric surfactants can contain the anionic or cationic group common in anionic or cationic surfactants and additionally can contain either hydroxyl or other hydrophilic groups that enhance surfactant properties. Such amphoteric surfactants include betaine surfactants, sulfobetaine surfactants, amphoteric imidazolinium derivatives and others.

Generally, the surfactant concentration ranges from about 1 wt. % to 50 wt. % and preferably from about 2 wt. % to 15 wt. %, by weight of the lubricant composition. One or more surfactants can be used.

The lubricant composition of the invention also generally includes a carrier. Water is the most commonly used and preferred carrier for carrying the various ingredients in the formulation of the lubricant composition. It is possible, however, to use a water-soluble solvent, such as alcohols and polyols such as ethanol, propanol, ethylene glycol, propylene glycol and the like, as well as mixtures. These solvents can be used alone or with water. The carrier is generally present in an amount of about 20 to about 95%, preferably 30–90%, more preferably 40–80% by weight of the composition. The lubricant composition can also be in the form of a concentrate to which the carrier is later added.

It is also desired to include water conditioning or chelating agent in the lubricant composition. Where water is used as carrier, there is a tendency for the hardness cations, such as calcium, magnesium, and ferrous ions to reduce the efficacy of the surfactants, and even form precipitates when coming into contact with ions such as sulfates and carbonates. Water conditioning agents can be used to form complexes with the hardness ions. Any such agents can be used. The preferable water conditioning agent is ethylene diamine tetracetic acid and its sodium salt, such as Versene sold by Dow Chemicals, diethylene triamine pentacetic acid, and sodium salt of nitrilotriacetic acid and N-hydroxyethylene diamine triacetic acid.

Generally the water conditioning agent is present in the range about 0.1% to 15% by weight of the lubricant composition, more preferably in the range of 1% to 5%.

In addition to the components described above, other components can be included with the lubricant to provide desired properties. For example, other antimicrobial agents besides the quaternary phosphonium, colorants, foam inhibitors, foam generators, PET stress cracking inhibitors, viscosity modifiers, friction modifiers, antiwear agents, extreme pressure agents, detergents, dispersants, corrosion inhibitors, and/or film forming materials can be used, each in amounts effective to provide the desired results.

Examples of useful antiwear agents and extreme pressure agents include zinc dialkyl dithiophosphates, tricresyl phosphate, and alkyl and aryl disulfides and polysulfides.

Examples of useful detergents and dispersants include alkylbenzene sulfonic acid, alkylphenols, carboxylic acids, alkylphosphonic acids and their calcium, sodium and magnesium salts, and polybutenylsuccinic acid derivatives.

Examples of useful foam inhibitors include methyl silicone polymers.

Useful additional antimicrobial agents (besides the phosphonium) include disinfectants, antiseptics and preservatives. Non-limited examples include phenols including halo- and nitrophenols and substituted bisphenols such as 4-hexylresorcinol, 2-benzyl-4-chlorophenol and 2,4,4'-trichlor-2'-hydroxydiphenyl ether, organic and inorganic acids and its esters and salts such as dehydroacetic acid, peroxycarboxylic acids, peroxyacetic acid, methyl p-hydroxy benzoic acid, cationic agents such as quaternary ammonium compound, aldehydes such as glutaraldehyde, antimicrobial dyes such as acridines, triphenylmethane dyes and quinones and halogens including iodine and chlorine compounds.

Also, the phosphonium compound can be used alone or in conjunction with an oxidizing and/or non-oxidizing anitmicrobial agent. Examples of useful oxidizing antimicrobial agents are $H_2O_2$, peracids, iodophors, chlorine dioxide, and interhalides. Examples of useful non-oxidizing antimicrobial agents include quaternary ammonium compounds, alkyl amines, phenolics, and tin and silver salts.

Non-limiting examples of useful foam generators include surfactants such as nonionic, anionic, cationic and amphoteric compounds.

Non-limiting examples of useful friction modifiers include fatty acids with 12–18 carbon atoms and fatty alcohols, esters of fatty acids such as glycerides, fatty amines and amides.

The lubricant composition of the invention can be used in any application where lubricity is desired. For example, the lubricant can be used to treat any type of container, including those mentioned in the Background section of this application. For example, glass or plastic containers, including polyethylene terephthalate containers, and metal containers, such as aluminum cans, papers, treated papers, coated papers, laminates, ceramics, and composites can be treated.

By container is meant any receptacle in which material is or will be held or carried. For example, beverage or solid or non-solid food and non-food containers are commonly used containers. Beverages include any liquid suitable for drinking, for example, fruit juices, soft drinks, water, milk, wine, artificially sweetened drinks, sports drinks, and the like. For example, containers used in the brewery, dairy, and food industry can be used. The lubricant provides excellent lubricity and detergency, as well as antimicrobial activity and non-corrosivity. If used in the beverage or food industry, the lubricant composition should be non-toxic and environmentally acceptable.

The lubricant can also be used to lubricate any conveyor where articles are intended to be conveyed as well as such articles. Examples of such articles include crates, carcasses, and mechanical parts.

Since the lubricant composition has high detergency and is non-corrosive, it can also be applicable to various cleaning applications such as in dishwasher detergents and car washes, and other applications requiring these properties.

The lubricant composition can be applied to a conveyor system surface that comes into contact with containers, the container surface that needs lubricity, or both. The surface of the conveyor that supports the containers may comprise fabric, metal, plastic, elastomer, composites, or mixture of these materials. Any type of conveyor system used in the field can be treated according to the present invention.

The lubricant composition can be applied in any desired manner, for example, by spraying, wiping, rolling, brushing, or a combination of any of these, to the conveyor surface and/or the container surface. If the container surface is coated, it is only necessary to coat the surfaces that come into contact with the conveyor, and/or that come into contact with other containers. Similarly, only portions of the conveyor that contacts the containers need to be treated.

The lubricant composition can provide a temporary or permanent coating on the container. A permanent coating is one that remains on the coated container during its life, whereas a temporary coating is one that can be or is removed during processing of the container or during its use. A temporary coating can be removed as desired, for example, by spraying with water.

The use of quaternary phosphonium is advantageous compared with amines because the amine compounds increase alkalinity of the system, and increase the likelihood of stress cracking in PET. The phosphonium does not have this disadvantageous property.

EXAMPLES

The invention can be better understood by the following examples. The examples are for illustration purposes only, and do not limit the scope of the invention.

Example 1

Antimicrobial Efficiency Measurement—Rate of Kill Test Results.

The rate of kill of a lubricating composition according to the invention (#2) and a comparative composition (#1) of the following compositions were tested.

| Material | Active % | #1 Quat. Am. Wt. % | #2 Quat. Phos. Wt. % |
|---|---|---|---|
| DI water | 100.00% | 65.1 | 57.6 |
| Tetrasodium EDTA PWD 4 $H_2O$ | 82.00% | 4.9 | 4.9 |
| Didecyl dimethyl ammonium chloride, 50% | 50.00% | 5 | 0 |
| Tolcide PS 200, 20% | 20.00% | 0 | 12.5 |
| Complex organo phosphate ester | 100.00% | 12.5 | 12.5 |
| Polyethylene phenol ether phosphate | 100.00% | 2.5 | 2.5 |
| Linear alcohol 60–70% ethoxylate | 100.00% | 8 | 8 |
| Sodium hydroxide 50% | 50.00% | 2 | 2 |
| TOTAL | | 100 | 100 |

The Rate of Kill Antimicrobial Efficiency Test was carried out according to the method described below:

The bacteria, staphylococus aureus ATCC6538 and enterobacter aerogenes ATCC 13048, were transferred and maintained on nutrient agar slants. Twenty-four hours prior to testing, 10 ml tubes of nutrient broth were inoculated with a loopful of each organism, to provide sufficient volume for testing. The inoculated nutrient broth cultures were incubated at 35 degrees C. Shortly before testing, equal volumes of both incubated cultures were mixed and used as the test inoculum.

The test solution was diluted to 0.5% wt. with sterile soft water. One ml of the inoculum was combined with 99 mls of the lubricant solution and swirled.

A one ml sample of the lubricant/inoculum mixture was removed after a 60 minute exposure time and added to 9 mls of a sterile chambers neutralizing broth. The neutralized sample was serially diluted with buffered water and plated in duplicate using TGE (tryptone glucose extract) neutralizing agar. The plates were incubated at 37 degrees C. for 48 hours then examined.

Controls to determine initial inoculum were prepared by adding one ml of inoculum to 99mls of buffered water, serially diluting the mixture with additional buffered water, and plating with TGE.

The % reduction and log reduction were calculated as:

% Reduction=[(# of initial inoculum−# of survivors)/(# of initial inoculum)]×100 where:

\# of initial inoculum=$3.4 \times 10^6$ CFU/ml

CFU/ml: Colony forming units/ml

Log Reduction=−[$\log_{10}$)(# of survivors/# of initial inoculum)]

A Log reduction of 1 indicates a 90% reduction of the microorganisms.

Log reduction at 0.5% concentration, 60 mins exposure

| Formula | Log reduction | |
|---|---|---|
| #1 | >6.26 | Quaternary ammonium containing lube for comparison (#1) |
| #2 | >6.26 | Quaternary phosphonium containing lube (#2) |

Example 1 indicates that the phosphonium-based composition has a significant kill efficiency.

Example 2

Effect of Combination of Fatty Acid and Quaternary Phosphonium on Antimicrobial Properties

| Stock solution: | | |
|---|---|---|
| Material | Active % | % solution |
| DI water | 100.00% | 70.1 |
| Tetrasodium EDTA PWD 4 H$_2$O | 82.00% | 4.9 |
| Complex organo phosphate ester | 100.00% | 12.5 |
| Polyethylene phenol ether phosphate | 100.00% | 2.5 |
| Linear alcohol 60–70% ethoxylate | 100.00% | 8 |
| Sodium hydroxide 50% | 50.00% | 2 |
| Total | | 100 |

To 25.0 g of the above solution was added:

| #1 | 0.63 g Tolcide PS 75, 0.68 g Oleic acid |
|---|---|
| #2 | 0.83 g Tolcide PS 75, 1.095 g Oleic acid |
| #3 | 1.17 g Tolcide PS 75, 0.63 g Oleic acid |

The solutions were tested by the same method described above for Example 1.

Log reduction at 0.5% concentration, 60 mins exposure

| Formula | Log reduction |
|---|---|
| #1 | >5.97 |
| #2 | >6.04 |
| #3 | >5.97 |
| Example- 1 #2 | >5.97 |

The above examples 1 and 2 demonstrate that the quaternary phosphonium containing lube showed an adequate kill as compared with the quaternary ammonium, and the addition of certain amount of oleic acid to the quaternary phosphonium lube did not reduce the kill. The later results are especially surprising because it would have been expected that the anionic oleic acid would interact with the cationic quaternary phosphonium and reduce the killing efficiency of the composition. This is because it known that oleic acid reduces the antimicrobial efficiency when combined with quaternary ammonium.

Example 3

Pet Bottle Stress Crazing/Cracking Test

PET 2 L bottles were charged with 1850 g of chilled water, 31.0 g of Na bicarbonate and 31.0 g of citric acid. The charged bottles were rinsed with DI water and set on clean paper towels for 6 hours.

Each of the charged bottles was then placed into a plastic bag containing 100 g of the testing solution and the bag was sealed. 3 bottles for each solution were prepared. The charged bottles sealed inside the bag were placed in a lined bin and aged at 43.3 degrees C., 50% RH in an environmental chamber. The base of the bottles was examined for craze after 65 hours aging.

| Results: | | | | | |
|---|---|---|---|---|---|
| Sample | Chemical | Wt. (g) in 100 g DI H2O | Active Compound | Wt. (g) of Active Compound | Base Appearance after Aging |
| #1 | Bardac 2250 (50%) | 0.09 | Didecyl dimethyl ammonium chloride | 0.045 | Bottle 1: crazed<br><br>Bottle 2: crazed<br>Bottle 3: crazed |
| #2 | Tolcide PS 200 (20%) | 0.225 | Tetrakishydroxy-methyl phosphonium sulphate | 0.045 | Bottle 1: no craze<br><br>Bottle 2: no craze<br>Bottle 3: no craze |

These results demonstrate that Tolcide PS 200 did not craze the PET bottle while Bardac did under the experimental condition, indicating that the quaternary phosphonium compound has less tendency than the quaternary ammonium to contribute to PET stress crazing.

Example 4

Beverage Compatibility Test

The beverage compatibility of the lubricant composition was determined as follows. The testing lubricants were diluted to 0.1% and/or 0.5% with soft water. The diluted lubricant was then mixed with a cola beverage at the ratios as indicated in the examples to prepare the lubricant-beverage combination. The mixture clarity was observed at time of 0 and 24 hours after the mixing. A cloudy mixture indicated an inadequate beverage compatibility.

| Formula of the invention: | | | | |
|---|---|---|---|---|
| Material | active % | % solution | RM wt g | solid wt g |
| DI water | 100% | 66.97% | 70.1 | |
| tetrasodium EDTA PWD 4 H2O | 82% | 4.68% | 4.9 | 4.02 |
| Tolcide PS75 | 75% | 4.46% | 4.67 | 3.5 |
| Oleic acid | 100% | 2.39% | 2.5 | 2.5 |
| complex organo phosphate ester | 100% | 11.94% | 12.5 | 12.5 |
| linear alcohol 60–70% ethoxylate | 100% | 7.64% | 8 | 8 |
| sodium hydroxide 50% | 50% | 1.91% | 2 | 1 |
| Total | | 100% | 104.67 | 31.52 |

The comparison product evaluation for comparison study was Dicolube RS 148 (an amine containing synthetic lube), commercially available from Diversey-Lever. Pepsi Cola was used for evaluation and soft water was used for lubricant dilution.

|  | Dicolube RS 148 0.5% | Formula of the Invention, 0.5% | Soft Water |
|---|---|---|---|
| Pepsi Cola | 30 ml | 30 ml | 30 ml |
| 0.5% lube | 10 ml | 10 ml |  |
| Soft water |  |  | 10 ml |
| Observation at 0 hr. | Cloudy | Clear | Clear |
| Observation at 24 hr. | Solid precipitated | Clear | Clear |

The results indicated that the beverage compatibility of the lubricant of the invention is superior to Dicolube RS 148.

The beverage compatability of the lubricating composition of the invention is shown below at various concentrations.

|  |  |  | Solution Clarity | | | | | |
|---|---|---|---|---|---|---|---|---|
|  |  | Lube | Soft Water | | 0.1% Lube | | 0.5% lube | |
|  | Bever- | (or | (control) | | | | | |
| Beverage | age ml | water) ml | At 0 hr. | At 24 hr. | At 0 hr. | At 24 hr. | At 0 hr. | At 24 hr. |
| Coke | 30 | 10 | Clear | Clear | Clear | Clear | Clear | Clear |
| Coke | 20 | 20 | Clear | Clear | Clear | Clear | Clear | Clear |
| Coke | 10 | 30 | Clear | Clear | Clear | Clear | Clear | Clear |
| Diet Coke | 30 | 10 | Clear | Clear | Clear | Clear | Clear | Clear |
| Diet Coke | 20 | 20 | Clear | Clear | Clear | Clear | Clear | Clear |
| Diet Coke | 10 | 30 | Clear | Clear | Clear | Clear | Clear | Clear |
| Pepsi | 30 | 10 | Clear | Clear | Clear | Clear | Clear | Clear |
| Pepsi | 20 | 20 | Clear | Clear | Clear | Clear | Clear | Clear |
| Pepsi | 10 | 30 | Clear | Clear | Clear | Clear | Clear | Clear |
| Mountain Dew | 30 | 10 | Clear | Clear | Clear | Clear | Clear | Clear |
| Mountain Dew | 20 | 20 | Clear | Clear | Clear | Clear | Clear | Clear |
| Mountain Dew | 10 | 30 | Clear | Clear | Clear | Clear | Clear | Clear |
| Minute Maid Orange | 30 | 10 | Clear | Clear | Clear | Clear | Clear | Clear |
| Minute Maid Orange | 20 | 20 | Clear | Clear | Clear | Clear | Clear | Clear |
| Minute Maid Orange | 10 | 30 | Clear | Clear | Clear | Clear | Clear | Clear |
| Root Beer | 30 | 10 | Clear | Clear | Clear | Clear | Clear | Clear |
| Root Beer | 20 | 20 | Clear | Clear | Clear | Clear | Clear | Clear |
| Root Beer | 10 | 30 | Clear | Clear | Clear | Clear | Clear | Clear |
| 7 Up | 30 | 10 | Clear | Clear | Clear | Clear | Clear | Clear |
| 7 Up | 20 | 20 | Clear | Clear | Clear | Clear | Clear | Clear |
| 7 Up | 10 | 30 | Clear | Clear | Clear | Clear | Clear | Clear |

The results of this table show that the quaternary phosphonium containing lube has an exceptional beverage compatibility and outperforms the comparison product.

Example 5
Effect of Adding Non-neutralized Oleic Acid on Lubricity.

The lubricity was tested as follows: Lubricity test was done by measuring the drag force (frictional force) of a weighted cylinder (228 g) riding on a rotating disc, wetted by the test sample. The material for the cylinder is mild steel and for the rotating disc is stainless steel, respectively. The drag force, using an average value, was measured with a solid state transducer, which is connected to the cylinder by a thin flexible string. The weight of the cylinder made from the same material is consistent for all the measurements.

The drag force is directly related to the friction coefficient of the lubrication. A higher drag force indicates a higher coefficient of friction or a poorer lubricity. A good lubricant would have a typical drag force less than 45.

|  | Active % | #1 RM wt g | #2 RM wt g | #3 RM wt g | #4 RM wt g |
|---|---|---|---|---|---|
| DI water | 100.0% | 70.10 | 70.1 | 70.10 | 70.10 |
| Tetrasodium EDTA PWD 4 H$_2$O | 82.0% | 4.90 | 4.9 | 4.90 | 4.90 |
| Tolcide PS75 | 75.0% | 3.32 | 3.32 | 3.32 | 4.00 |
| Oleic acid |  |  | 2.52 | 4.38 | 3.76 |
| Complex organo phosphate ester | 100.0% | 12.50 | 12.5 | 12.50 | 12.50 |
| Polyethylene phenol ether phosphate | 100.0% | 2.50 | 2.5 | 2.50 | 2.50 |
| Linear alcohol 60–70% ethoxylate 7 | 100.0% | 8.00 | 8 | 8.00 | 8.00 |
| Sodium hydroxide 50% | 50.0% | 2.00 | 2 | 2.00 | 2.00 |
| Total |  | 103.32 | 105.84 | 107.70 | 107.76 |

Lubricity test results of the solution at 0.1% conc. In soft water

| Frictional force (g) | #1 | #2 | #3 | #4 |
|---|---|---|---|---|
| Minimum | 33.4 | 29 | 29.3 | 28.1 |
| Maximum | 45.7 | 32.8 | 33 | 31.8 |
| Average | 39.6 | 30.9 | 31.2 | 30 |

This example shows that the addition of oleic acid significantly increased the mild steel on stainless steel lubricity.

Example 6

Effect of Neutralization of Oleic Acid on Alkalinity of the Lubricant.

The testing solutions were diluted to 1.0% with DI water then titrated with 0.1N HC1. The total alkalinity was calculated by:

$$\% \text{ alkalinity as } CaCO_3 = \frac{(\text{mls HCl to ph 4.0})(N \text{ HCl})}{(g \text{ sample titrated})} \times \frac{100.1}{2} \times \frac{100}{1000}$$

| Material | active % | solution A RM wt (g) | solution B RM wt (g) | solution C RM wt (g) |
|---|---|---|---|---|
| DI water | 100.0% | 35.05 | 32.33 | 22.22 |
| Tetrasodium EDTA PWD 4 H2O | 82.0% | 2.45 | 2.45 | 2.45 |
| Tolcide PS75 | 75.0% | 2.34 | 2.34 | 2.34 |
| Oleic acid | 100.0% | 1.25 | 0.00 |  |
| Oleic acid neutralized with NaOH* | 8.9% |  |  | 14.08 |
| complex organo phosphate ester | 100.0% | 6.25 | 6.25 | 6.25 |
| linear alcohol 60–70% ethoxylate | 100.0% | 4.00 | 4.00 | 4.00 |
| sodium hydroxide 50% | 50.0% | 1.00 | 1.00 | 1.00 |

*Oleic acid was neutralized with NaOH as follows:
10.0 g (0.0354 moles) of oleic acid in 100 g of DI was neutralized with 2.65 g (0.0331 moles) of 50% NaOH to result in a clear solution with pH = 9.65.

Results of alkalinity analysis:

| Solution | | Alkalinity as CaCO$_3$ At 1% of conc. Lube (ppm) |
|---|---|---|
| A | With Non-neutralized oleic acid | 80.5 |
| B | With No oleic acid | 90.0 |
| C | With Neutralized oleic acid | 121.5 |

This example demonstrates alkalinity was reduced by non-neutralized oleic acid The alkalininity of solution C does not conform to current guidelines of less than 100 ppm. It is desirable to reduce alkalinity because alkalinity is known to decompose PET.

Example 7
Effect of Adding Fatty Acid on Solution Stability:

| Material | Active % | #1 Wt. % | #2 Wt. % |
|---|---|---|---|
| DI water | 100.00% | 65.1 | 57.6 |
| Tetrasodium EDTA PWD 4 H2O | 82.00% | 4.9 | 4.9 |
| didecyl dimethyl ammonium chloride, 50% | 50.00% | 5 | 0 |
| Tolcide PS 200, 20% | 20.00% | 0 | 12.5 |
| complex organo phosphate ester | 100.00% | 12.5 | 12.5 |
| Polyethylene phenol ether phosphate | 100.00% | 2.5 | 2.5 |
| linear alcohol 60–70% ethoxylate | 100.00% | 8 | 8 |
| sodium hydroxide 50% | 50.00% | 2 | 2 |
| | total | 100 | 100 |

0.7 g of oleic acid was added to 25.0 g of the above solutions and mixed, then the mixture appearance was examined:

| #1 | Cloudy and phase separation appeared |
|---|---|
| #2 | Clear |

This example demonstrates that adding certain amount of fatty acid to the phosphonium based lube does not create a phase separation, whereas with the ammonium based lube phase separation occurred.

The materials used in the above examples are shown in the following Table:

| Function | Chemical Name | Trade Name | Vendor |
|---|---|---|---|
| Carrier | DI water | | |
| Chelating agent | Tetrasodium EDTA PWD 4 H$_2$O | Versene (R) 220 | Dow Chem. |
| Antimicrobial agent | Tetrakishhydroxymethyl phosphonium sulphate, 75% in water | Tolcide PS75 | Albright and Wilson |
| Antimicrobial agent | Tetrakishhydroxymethyl phosphonium sulphate, 20% in water | Tolcide PS200 | Albright and Wilson |
| Lubricating agent | Oleic acid | Emersol 213 | Henkel |
| Lubricating agent and detergent | Complex organo phosphate ester | Emphos PS-236 | Witco |
| Detergent | linear alcohol 60–70% ethoxylate | Neodol 25 - 7 | Shell |
| Neutralizer | sodium hydroxide 50% | | |
| Antimicrobial agent | Didecyl dimethyl ammonium chloride | Bardac 2250 | Lonza |
| Detergent and lubricating agent | Polyethylene phenol ether phosphate | | Rhone-Poulenc |

The invention provides use of quaternary phosphonium compounds in a beverage lubricant sufficient to provide antimicrobial properties, good PET compatibility, and beverage compatibility and retained good product stability even if a non-neutralized fatty acid is used.

It has also been found that using non-neutralized fatty acid as a lubricating agent, not only significantly enhances the universal lubricity, but also reduces the alkalinity of the lubricant. Hence reduction in PET bottle stress cracking is anticipated.

Moreover, it has been found that the addition of a fatty acid to the quaternary phosphonium lubricant does not alter the concentrated solution stability. In contrast, a phase separation often results while adding the fatty acid to quaternary ammonium containing lubricants.

It is believed that Applicants' invention includes many other embodiments, which are not herein described, accordingly this disclosure should not be read as being limited to the foregoing examples or preferred embodiments.

What we claim is:

1. A container or a conveyor for a container, whose surface is coated at least in part with a lubricant composition comprising a lubricating agent and an antimicrobial effective amount of a quaternary phosphonium compound.

2. A container or conveyor as claimed in claim 1, wherein the composition comprises water as a carrier.

3. A container or conveyor as claimed in claim 1, wherein the lubricating agent comprises a non-neutralized fatty acid.

4. A container or conveyor as claimed in claim 3, wherein the non-neutralized fatty acid comprises oleic acid or tall oil fatty acid.

5. A container or conveyor as claimed in claim 1, wherein the quaternary phosphonium compound comprises a phosphonium sulfate.

6. A container or conveyor as claimed in claim 1, wherein the container is a beverage container.

7. A container or conveyor as claimed in claim 6, wherein the portions of the container's surface that are intended to come into contact with a conveyor system are treated with the lubricant composition.

8. A container or conveyor as claimed in claim 6, wherein the container is made from polyethylene terephthalate.

9. A process for lubricating a container, comprising applying to at least a portion of a surface of the container, a lubricant composition comprising a lubricating agent and an antimicrobial effective amount of a quaternary phosphonium compound.

10. A process as claimed in claim 9, wherein the applying comprises coating the portions of the container that come into contact with other containers or the conveyor with the lubricant composition.

11. A process as claimed in claim 9, wherein a conveyor is coated with the lubricant composition, whereby the lubricant composition on the conveyor system is applied to the container while the container is on the conveyor system.

12. A process for lubricating a conveyor, comprising applying to at least a portion of the conveyor, a lubricant composition comprising a lubricating agent and an antimicrobial effective amount of a quaternary phosphonium compound, and then moving a container on the conveyor.

13. A lubricant composition comprising a lubricating agent and an antimicrobial effective amount of a quaternary sulfonium or quaternary iodonium compound.

14. A lubricant composition comprising a phosphate ester lubricating agent and an antimicrobial effective amount of a quaternary phosphonium compound.

15. A lubricant composition comprising a fatty acid lubricating agent and an antimicrobial effective amount of a quaternary phosphonium compound.

16. A lubricant composition as claimed in claim 15, wherein the fatty acid comprises a non-neutralized fatty acid.

17. A lubricant composition as claimed in claim 16, further comprising a phosphate ester lubricating agent.

18. A lubricant composition comprising an amine lubricating agent and an antimicrobial effective amount of a quaternary phosphonium compound.

19. A lubricant composition comprising a quaternary phosphonium compound and a quaternary ammonium compound.

20. A method of preventing or reducing stress cracking of polyethylene terephthalate containers comprising treating the container with a lubricating composition comprising a lubricating agent and a quaternary phosphonium compound.

21. A beverage lubricant comprising a quaternary phosphonium compound.

22. A lubricant composition comprising a quaternary phosphonium compound and one or more of an oxidizing antimicrobial agent and a non-oxidizing antimicrobial agent.

23. A container or conveyor as claimed in claim 1, wherein the phosphonium compound is selected from the group consisting of tetrakis (hydroxymethyl) phosphonium sulfate, tetrabutyl phosphonium bromide, tetrabutyl phosphonium chloride, tributyl (tetradecyl) phosphonium chloride, trioctyl (octadecyl) phosphonium iodode, and tetrakis (hydroxymethyl) phosphonium chloride.

24. A process as claimed in claim 9, wherein the phosphonium compound is selected from the group consisting of tetrakis (hydroxymethyl) phosphonium sulfate, tetrabutyl phosphonium bromide, tetrabutyl phosphonium chloride, tributyl (tetradecyl) phosphonium chloride, trioctyl (octadecyl) phosphonium iodode, and tetrakis (hydroxymethyl) phosphonium chloride.

25. A lubricant composition comprising about 0.5 to about 25 weight percent of a phosphonium compound, about 0.1 to about 20 percent by weight of a fatty acid, about 1 to about 50 percent by weight of a phosphate ester, a neutralizing agent in an amount effective to provide the composition with a pH of about 3 to about 9.5, about 0.5 to about 30 percent by weight of a nonionic surfactant, and water as a carrier, the percents based on the total weight of the composition.

26. A lubricant composition comprising 2 to 10 weight percent of a phosphonium compound, 0.5 to 7 percent by weight of a fatty acid, 5 to 25 percent by weight of a phosphate ester, a neutralizing agent in an amount effective to provide the composition with a pH of 5.5 to 7.5, 2 to 10 percent by weight of a nonionic surfactant, and water as a carrier, the percents based on the total weight of the composition.

27. An object or a conveyor for an object, whose surface is at least temporarily coated at least in part with a lubricant composition comprising a lubricating agent and an antimicrobial effective amount of a quaternary phosphonium compound.

28. A lubricant composition as claimed in claim 15, wherein the fatty acid is partially neutralized.

* * * * *